United States Patent [19]

Sopeña Quesada

[11] 4,353,363
[45] Oct. 12, 1982

[54] INTRAUTERINE SPERMICIDE

[76] Inventor: Angel Sopeña Quesada, C/Chapineria, 6, Madrid 35, Spain

[21] Appl. No.: 229,670

[22] Filed: Jan. 29, 1981

Related U.S. Application Data

[63] Continuation of Ser. No. 20,234, Mar. 13, 1979, abandoned.

[30] Foreign Application Priority Data

Nov. 23, 1978 [ES] Spain ..................................... 239.677

[51] Int. Cl.³ .............................................. A61F 5/46
[52] U.S. Cl. .................................................. 128/130
[58] Field of Search ................ 128/130, 127, 131, 260

[56] References Cited

U.S. PATENT DOCUMENTS

| | | | |
|---|---|---|---|
| 3,563,235 | 9/1968 | Zipper | 128/130 |
| 3,678,927 | 7/1972 | Soichet | 128/130 |
| 3,803,308 | 4/1974 | Zipper | 128/130 |
| 3,834,378 | 9/1974 | Lerner et al. | 128/130 |
| 3,913,573 | 10/1975 | Gutmiele | 128/130 |
| 3,937,217 | 2/1976 | Kosonen | 128/130 |
| 4,018,220 | 4/1977 | Emmett | 128/130 |
| 4,026,281 | 5/1977 | Mayberry et al. | 128/130 |
| 4,038,978 | 8/1977 | Morris et al. | 128/130 |
| 4,040,417 | 8/1977 | Zipper | 128/130 |
| 4,117,838 | 10/1978 | Hasson | 128/130 |

Primary Examiner—Kyle L. Howell
Assistant Examiner—C. W. Shedd
Attorney, Agent, or Firm—Wenderoth, Lind & Ponack

[57] ABSTRACT

An intrauterine spermicide includes a support body onto which is wound a copper spiral acting as a spermicide. The support body has extending therefrom two arched arms which are oriented to extend toward the oviducts. Each of the arms has at its free end a copper mass which is housed in the tip of the respective oviduct.

2 Claims, 16 Drawing Figures

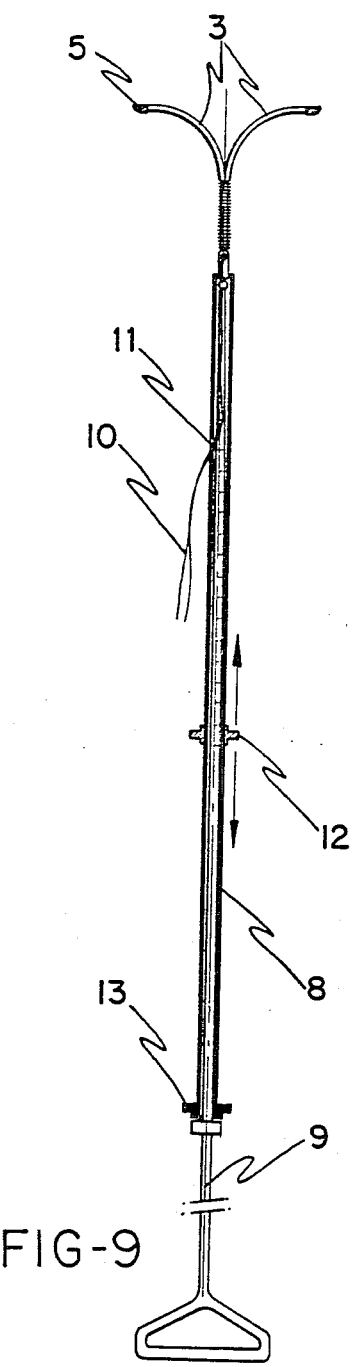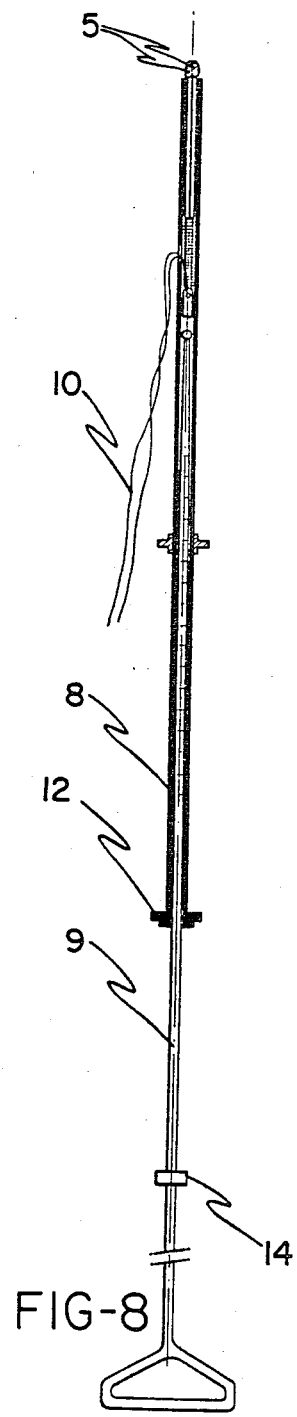

INTRAUTERINE SPERMICIDE

This is a continuation application of Ser. No. 6/020234, filed Mar. 13, 1979 now abandoned.

BACKGROUND OF THE INVENTION

The present invention relates to an intrauterine device useful to prevent conception.

Spermicides of this type, constituted by a support body onto which a copper spiral acting as the spermicide is wound, are known.

The main feature of this invention, which departs from conventional devices, resides in the existence of two diametrically opposed arched arms which extend from a support body, each arm having joined to the free end thereof a copper cap to be housed in the top of the corresponding oviduct of the user.

The main object of the invention is to obtain a greater degree of safety of the spermicide and the conception preventing function thereof, since it creates a second barrier at the level of the entrance to the oviducts, and thus considerably reduces the risk of spermatozoa having access thereto and consequently the risk of fertilization of the ovum, or its implantation in the tip of the oviduct where this normally takes place.

The device of the invention offers a greater adaptability to the uterus, since the shape thereof is adaptable to that of the uterine cavity, such that the device is capable of implantation in a fallen uterus.

Greater case of insertion is also obtained, thereby eliminating the need for use of sterilized material, such as gloves, and the carrying out of difficult manipulations during implantation, as is required with conventional devices.

BRIEF DESCRIPTION OF THE DRAWINGS

To complement the description which will subsequently be made and for a better understanding of the characteristics of the invention, reference will be made to the accompanying drawings, wherein:

FIG. 8 is a view of the assembly of the FIG. 7 in a mounted condition.

FIG. 9 is a view similar to FIG. 8 of the assembly in the semi-release position of the spermicide.

DETAILED DESCRIPTION OF THE INVENTION

Figures 1, 2:
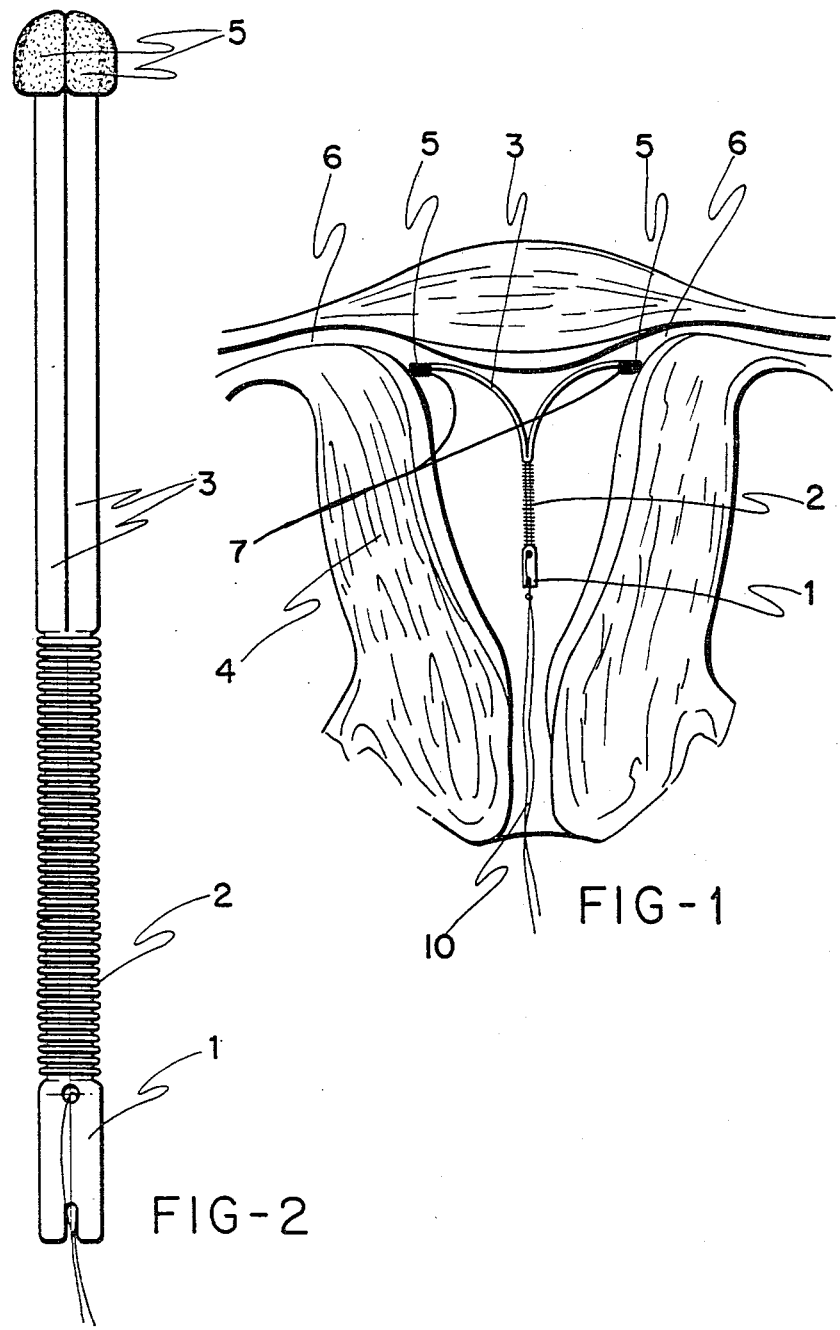
FIG. 1 is a schematic view of the device of the invention, shown inserted in a uterine cavity.
FIG. 2 is a side elevational view of the device, shown housed in an inserter tube.

As can be seen from the mentioned figures, the device is constituted by a support body 1 onto which a copper spiral 2 is wound. From one of the ends of this support body 1 there extend arched arms 3, semi-cylindrical in section and of a flexible material, so that, due to the flexibility thereof, they can be joined to form a cylindrical body as shown in FIG. 2, for the insertion thereof into a uterus 4.

Each one of these arms 3 has at its free end a mass of copper 5 which cooperates with the spiral 2.

Thus, the spiral 2 occupies the uterus cavity, while the copper masses 5 will be housed in the tips of the oviducts 6 and thus perform their spermicide function on the spermatozoa which have been able to bypass the barrier formed by the spiral 2 and thereby further prevent implantation of an ovum.

The structure of the arched flexible arms is such that, in the folded position corresponding to the inserting position thereof, it has in general, a diameter approximately equal to the outer diameter of the spiral 2. The end copper masses 5 together have the shape of a semi-spherical cap which is slightly stepped with respect to the remainder of the device in order to form an abutment for an inserter tube.

Figure 3:
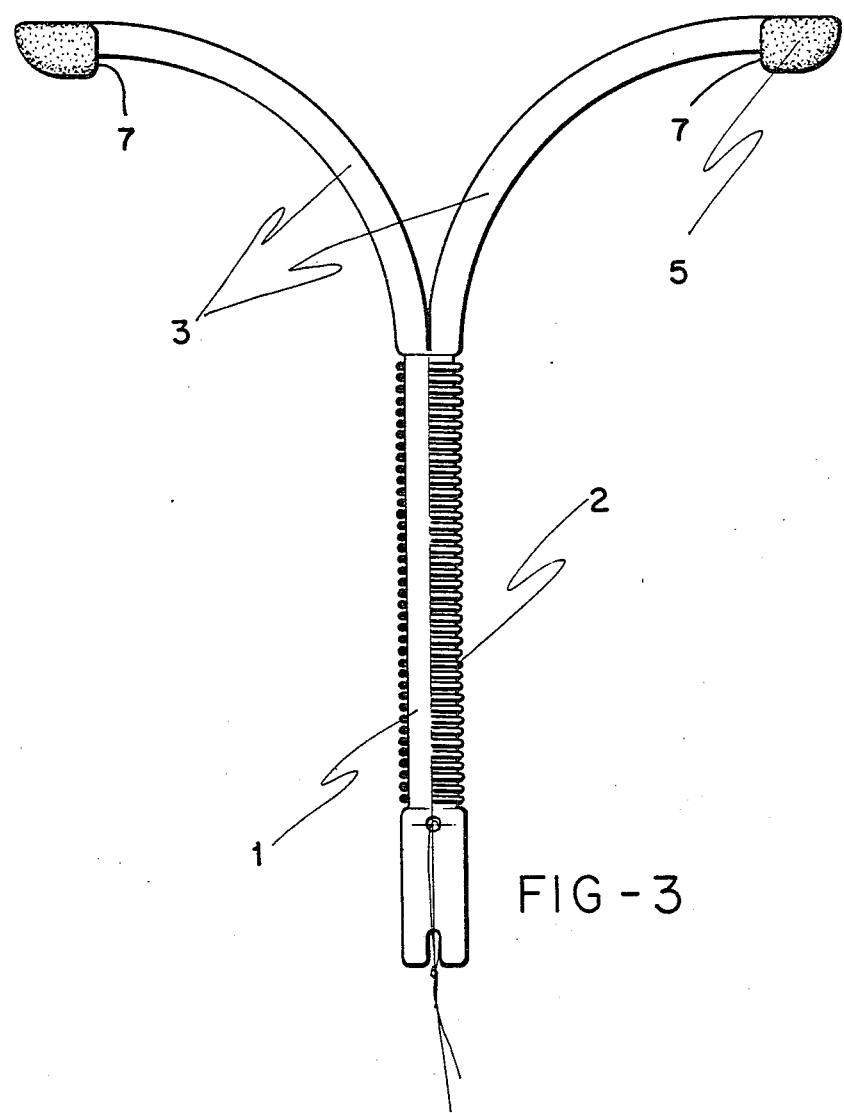
FIG. 3 is a side elevational view of the device, once implanted, the copper spiral being shown in a quarter section.
Figure 4:
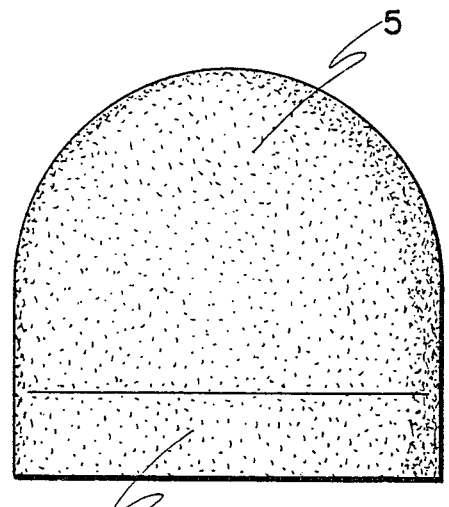
FIG. 4 is an elevational view of one of the copper masses which are solidly attached to the free ends of the arms.
Figure 5:
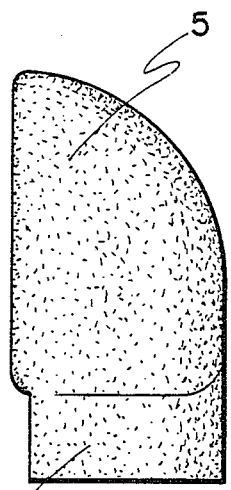
FIG. 5 is a side view of the copper mass of FIG. 4.
Figure 6:
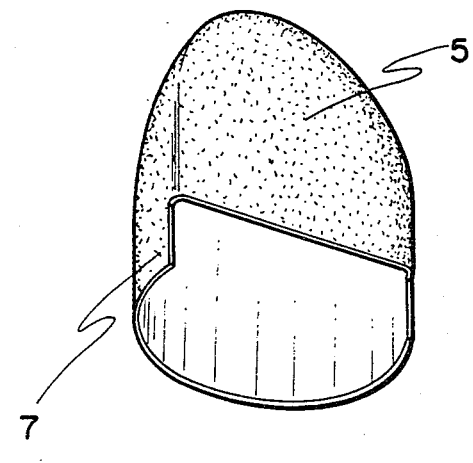
FIG. 6 is a perspective view of the copper mass.
Figure 7:
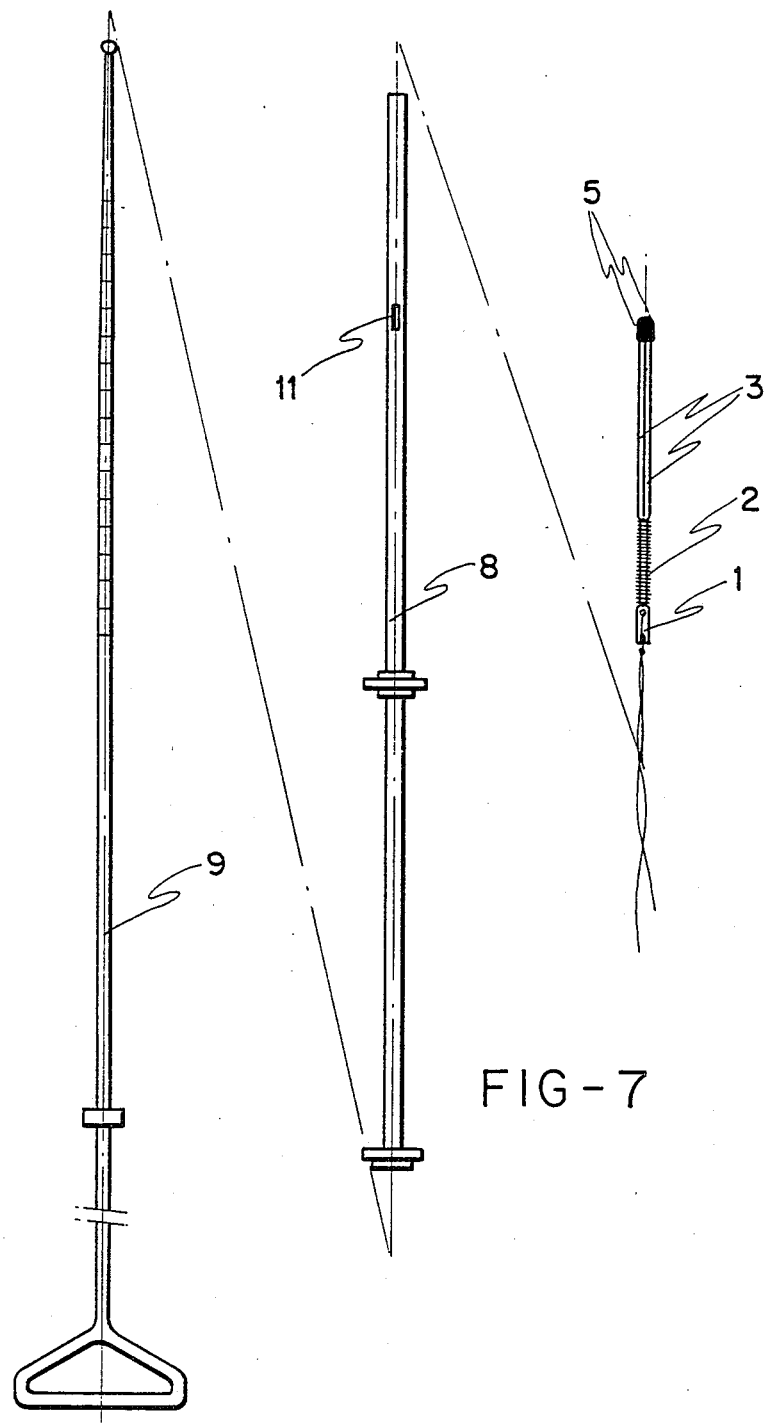
FIG. 7 is an expanded view of the intrauterine spermacide assembly of the invention with the component parts of an inserter tube and hysterometer for implanting the same.
Figure 10:
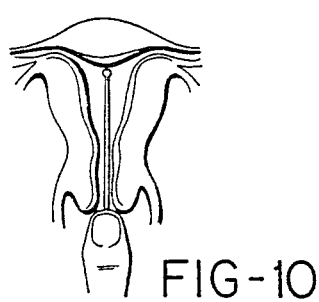
FIGS. 10, 11, 12, 13, 14, 15 and 16 are schematic views illustrating the different operative phases corresponding to the insertion of the spermicide in the uterus.
Figure 11:
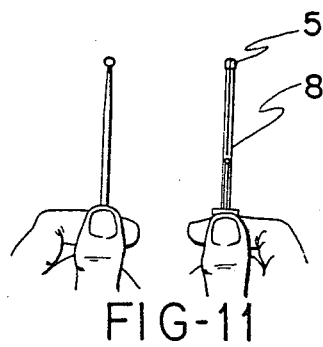
Figure 12:
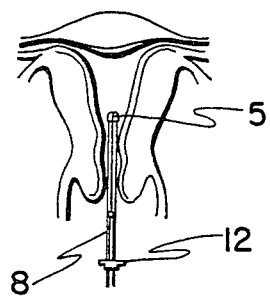
Figure 13:
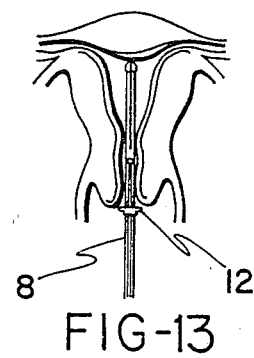
Figure 14:
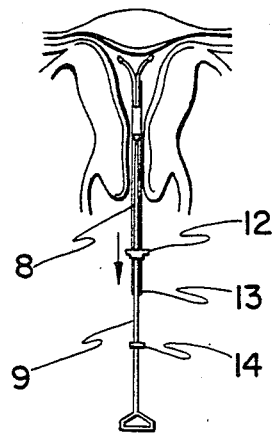
Figure 15:
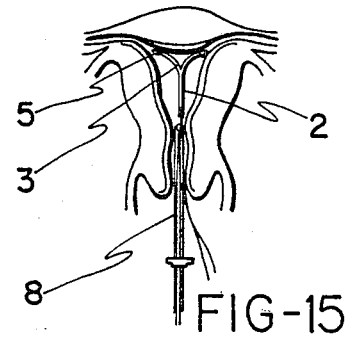
Figure 16:
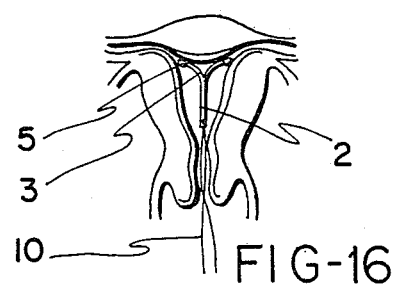

According to the preferred embodiment, this configuration in the form of a substantially hemi-spherical cap of the copper masses which occupy the end zones of the arms 3, also applies to the arms, with each copper mass only constituting a cover which is attached to the respective end of the arm 3 and which is fixed thereto by folding over or crimping the coupling edge 7 as can be seen by comparing FIGS. 1 and 3 with FIGS. 4–6.

The device is inserted by means of a mechanism including an inserter tube 8 and a thrust plunger 9 which, in turn, can be used as a hysterometer. The spermicide is housed inside of the inserter tube 8 and together therewith is inserted into the uterine cavity. The inserter tube 8 is then extracted while the thrust plunger 9 maintains the spermicide inside the uterus.

The spermicide is housed in the inserter tube 8 by folding arms 3 in directions opposite to the flexible nature of the material of the arms, until the position shown in FIGS. 2 and 8 is reached. This position is maintained, due to the tubular nature of the inserter 8, by tightening a thread 10 which is fixed to the end of the device and which projects outwardlay through a groove 11 in the inserter tube.

When the inserter tube 8 is withdrawn from the uterus, the spermicide is maintained in the interior by the thrust plunger 9. The tube 8 is withdrawn progressively by the device, whereby the arms 3 adopt the arched configuration or stable position, and the copper masses 5 are directed towards the tips of the oviducts 6, as shown in FIG. 1.

FIGS. 10 to 16 clearly illustrate the process of inserting the spermicide. First, the depth of the uterus is measured, which is reflected in the inserter tube 8 through the movable butt 12 which rests at the mouth of the uterus. When the spermicide is mounted in the inserter tube, along with the hysterometer 9, it is inserted in the uterus to the level determined by the movable butt 12. At this time the hysterometer 9 is maintained stationary and the inserter tube is withdrawn until a fixed butt 13 of the tube rests on a fixed butt 14 of the hysterometer, at which time the arms 3 of the spermicide expand and the inserter can be completely withdrawn.

It can be seen from the above that the device can be inserted rapidly and easily. Unintentional withdrawal of the device is practically impossible since the arms 3 thereof act to retain the device in place.

The copper surface forming the spermicide has a surface area of 300 mm$^2$, 240 mm$^2$ of which correspond to the spiral 2, while the remaining 60 mm$^2$ correspond to the masses 5 housed in the oviducts.

I claim:

1. An intrauterine spermicide comprising:

an elongated cylindrical support body adapted to be positioned within a uterine cavity;

said support body having extending from an end thereof two arms adapted, when said support body is positioned in the uterine cavity, to extend in the directions of the oviducts, each said arm having a semi-cylindrical cross-sectional configuration;

each said arm extending away from said support body in a curved manner to form a configuration approximately corresponding to a quarter of the circumference of a circle, such that said two arms together form a curved V-shaped configuration extending away from said support body and adaptable without being rejected to a fallen uterus;

said support body having a reduced diameter portion forming an annular recess;

a copper wire wound as a spiral around said reduced diameter portion and acting as a spermicide;

the depth of said recess substantially corresponding to the thickness of said copper wire; and each said arm having at the free end thereof a copper mass forming a spermicide for spermatozoa which have bypassed said copper wire.

2. An intrauterine spermicide as claimed in claim 1, wherein each said copper mass has a semi-cylindrical cross-sectional configuration of a size larger than the respective said arm, said two copper masses together forming, when said two arms are folded together in an inserting position, a hemi-spherical cap, and each said copper mass being attached to the free end of the respective said arm by folding of a coupling edge of said copper mass.

* * * * *